(12) United States Patent
Paraschiv et al.

(10) Patent No.: US 8,814,870 B2
(45) Date of Patent: Aug. 26, 2014

(54) HOOK SHAPED ULTRASONIC CUTTING BLADE

(75) Inventors: Mircea Paraschiv, Nesconset, NY (US); Theodore A. D. Novak, Northport, NY (US); Alexander L. Darian, Huntington Station, NJ (US); Ronald R. Manna, Valley Stream, NY (US)

(73) Assignee: Misonix, Incorporated, Farmingdale, NY (US)

( * ) Notice: Subject to any disclaimer, the term of this patent is extended or adjusted under 35 U.S.C. 154(b) by 1519 days.

(21) Appl. No.: 11/452,608

(22) Filed: Jun. 14, 2006

(65) Prior Publication Data

US 2008/0009848 A1    Jan. 10, 2008

(51) Int. Cl.
*A61B 17/32* (2006.01)

(52) U.S. Cl.
CPC ............. *A61B 17/320068* (2013.01); *A61B 2017/320076* (2013.01)
USPC .............................................. 606/79

(58) Field of Classification Search
USPC .......................... 606/79, 167–173; 604/22; 433/118–119, 86; 30/44–45
See application file for complete search history.

(56) References Cited

U.S. PATENT DOCUMENTS

| | | | |
|---|---|---|---|
| 2,838,049 A * | 6/1958 | Eisenhofer et al. ........... | 606/167 |
| 2,874,470 A * | 2/1959 | Richards ...................... | 433/85 |
| 3,526,219 A * | 9/1970 | Balamuth .................... | 600/565 |
| 3,844,272 A * | 10/1974 | Banko ........................ | 600/566 |
| 4,099,529 A * | 7/1978 | Peyman ...................... | 606/171 |
| 4,542,741 A * | 9/1985 | Burgin ........................ | 606/167 |
| 4,655,215 A * | 4/1987 | Pike ............................ | 606/42 |
| 4,832,683 A * | 5/1989 | Idemoto et al. ............. | 604/22 |
| 5,135,528 A * | 8/1992 | Winston ...................... | 606/79 |
| 5,167,725 A | 12/1992 | Clark et al. | |
| 5,188,102 A * | 2/1993 | Idemoto et al. ............. | 604/22 |
| D340,981 S * | 11/1993 | Hood et al. ................. | D24/146 |
| D344,799 S * | 3/1994 | Hood et al. ................. | D24/144 |
| D346,024 S * | 4/1994 | Hood et al. ................. | D24/144 |
| 5,318,570 A | 6/1994 | Hood et al. | |
| 5,324,299 A * | 6/1994 | Davison et al. ............. | 606/167 |
| 5,346,502 A * | 9/1994 | Estabrook et al. .......... | 606/169 |
| 5,397,333 A * | 3/1995 | Knoepfler ................... | 606/170 |
| 5,417,654 A * | 5/1995 | Kelman ...................... | 604/22 |
| 5,776,092 A * | 7/1998 | Farin et al. .................. | 604/22 |
| 5,807,392 A * | 9/1998 | Eggers ........................ | 606/31 |
| 5,807,401 A * | 9/1998 | Grieshaber et al. .......... | 606/107 |
| 5,906,628 A | 5/1999 | Miyawaki et al. | |
| 5,935,142 A * | 8/1999 | Hood ........................... | 606/169 |
| 6,117,152 A * | 9/2000 | Huitema ...................... | 606/169 |
| 6,254,622 B1 * | 7/2001 | Hood ........................... | 606/169 |
| 6,379,371 B1 | 4/2002 | Novak | |
| 6,436,115 B1 * | 8/2002 | Beaupre ...................... | 606/169 |
| 6,443,969 B1 | 9/2002 | Novak | |
| 6,497,715 B2 * | 12/2002 | Satou ........................... | 606/169 |

(Continued)

FOREIGN PATENT DOCUMENTS

WO    WO94/21183    9/1994
WO    WO99/42040    8/1999

*Primary Examiner* — Mary Hoffman
(74) *Attorney, Agent, or Firm* — R. Neil Sudol; Henry D. Coleman

(57) ABSTRACT

An ultrasonic surgical blade has a blade body and a shank. The shank is fixed at one end to the blade body and is operatively connectable at an opposite end to a source of ultrasonic vibrations. The shank has a longitudinal axis. The blade body is eccentrically disposed relative to the axis.

19 Claims, 1 Drawing Sheet

(56) References Cited

U.S. PATENT DOCUMENTS

| | | |
|---|---|---|
| 6,695,847 B2 | 2/2004 | Bianchetti et al. |
| 6,830,555 B2 * | 12/2004 | Rockley et al. ............ 604/22 |
| 6,863,672 B2 | 3/2005 | Reiley et al. |
| 7,044,736 B2 * | 5/2006 | Atkin et al. ............ 433/119 |
| 7,066,923 B2 * | 6/2006 | Tjia ............ 604/500 |
| 7,094,229 B2 * | 8/2006 | Boukhny et al. ............ 604/500 |
| 7,135,029 B2 * | 11/2006 | Makin et al. ............ 606/169 |
| 7,217,128 B2 * | 5/2007 | Atkin et al. ............ 433/119 |
| 2004/0133229 A1 | 7/2004 | Lambrecht et al. |
| 2006/0271077 A1 * | 11/2006 | Graser ............ 606/167 |
| 2010/0010526 A1 * | 1/2010 | Mitusina ............ 606/171 |

\* cited by examiner

HOOK SHAPED ULTRASONIC CUTTING BLADE

FIELD OF THE INVENTION

This invention relates to an ultrasonic cutting blade. The blade is particularly useful in a surgical application to cut tissue such as cartilage and bone.

BACKGROUND OF THE INVENTION

In the field of orthopedics, the cutting of living bone is a prerequisite for many procedures. Such procedures include the reconstruction of damaged tissue structures due to accidents, the grafting of healthy bone into areas damaged by disease, or the correction of congenital facial abnormalities like a receding chin line. Over several centuries, these tasks were performed through the utilization of devices called bone saws.

Traditional bone saws are categorized into several basic categories. Hand powered saws or drills are just that, hand held devices which require the operator to move the device in a fashion similar to that used for carpentry tools. Powered devices, whether electric or pneumatic, are of either the reciprocating or rotary type. The reciprocating devices use a flat, sword like blade where the back and forth motion is provided by a motor instead of the hand. The rotary devices use a rotating motor to spin a drill bit or a blade which has teeth arranged around its circumference similar to a table saw blade. All of these traditional bone saws are used today in medical procedures around the world.

While traditional saws are functional, they have many disadvantages. With either the band or reciprocating saws, for instance, it is not easy to initiate and direct a cut. A cut must start from an edge or, alternatively, a starting hole must be used. To create a starting hole, a drill or similar instrument is operated to bore into the bone. Subsequently, a cutting blade is inserted into the bored hole. The user can then proceed to cut. Alternatively, a rotary type blade may be used. However, when a rotary blade is used, the cut must follow a relatively straight path to prevent the blade from binding in the cut. With all blades the ability to create a curved or compound angle cut is extremely limited by the blade chosen. The relatively thick blades have a wide kerf; so that a significant thickness of the viable bone is lost in the cutting procedure. Physicians would like this width to be as thin as possible in most procedures where reconstruction is necessary.

Above all, the relatively slow linear or tangential speeds of conventional bone saw blades coupled with the teeth necessary for cutting result in high frictional losses, which becomes manifested as heat. Heat will cause necrosis of the tissue if the bone temperatures reach 47° C. for more than a few seconds. When tissue necroses, the bone recedes after the surgery as the necrotic bone is overgrown. During such natural post-surgical tissue developments, the thickness of the cuts in the bone actually increases. The bone rescission process must be complete before healing can begin. To prevent the shortening of the length of the bone, metal plates and screws are used to fix the bone fragments in proper position. All of these factors obviously lead to increased operative time, and more importantly, to dramatically increased healing time, since the bone must knit across a greater span. Some studies have shown the strength of the bone to be effected negatively as well.

When an upper or lower jaw is to be cut in elective surgery, the heating effect of traditional saws requires even more extraordinary intervention to prevent damage. Cutting the jaw between the teeth will cause loss of teeth if the bone is damaged or does not heal quickly. To prevent the tooth loss, the teeth must be spread apart preoperatively; sometimes forcing the patient to wear braces for up to 6 months before the operation can take place. In these cases, the costs and patient discomfort increases dramatically.

To limit the tissue temperature rise in an attempt to reduce necrosis, some traditional surgical saws provide cooling liquid to the surgical site. See, for instance, U.S. Pat. No. 4,008,720 to Brinckmann et al. These devices typically introduce coolant into spaces between segments on the cutting edge or rely on spray methods to flood the cutting site with fluid. Another technique employed by clinicians is to make very light cuts and increase the time between passes of the tool. Coupled with irrigation of the area, bone temperature rise is reduced measurably. Of course, this technique increases operative time and clinician fatigue.

Several researchers have proposed the use of ultrasonic tools for bone separation. The use of ultrasonic surgical instruments for cutting through various tissues is well known. While these devices are superior to the traditional saws in several aspects such as reduced kerf size, reduced noise, and superior ability for making complex geometric cuts, the temperature rise in bone due to frictional heating at the blade/tissue interface is still a significant problem. The problem is exacerbated with the use of ultrasonics due to the rapid motion involved as compared to that of traditional reciprocating saws. Some designers have tried to reduce heating by modifying the cross-section of the cutting blade. U.S. Pat. No. 5,188,102 to Idemoto, U.S. Pat. No. 4,188,952 to Loschilov, and U.S. Pat. No. 5,261,922 to Hood all show designs for cutting which have modified cross sections to reduce frictional heating.

Several ultrasonic devices have provided cooling to the cutting blade with varied degrees of success. U.S. Pat. No. 4,823,790 to Alperovich et al. shows a design for a cryogenically cooled scalpel blade. However, this design may actually damage viable tissue by freezing. In addition, this design does not provide any coolant to surrounding tissue not in direct contact with the blade.

U.S. Pat. Nos. 5,205,817, 5,188,102, and 4,832,683 all to Idemoto show examples of ultrasonic instruments with provisions for fluid cooling. These instruments, however, either do not provide optimal coolant flow where it is needed, mainly at the cutting portion of the blade, or for ones that do provide coolant at the tip, they interrupt the cutting edge with holes for the coolant. An interrupted, uneven cutting edge hinders manipulation and makes it difficult to guide the blade on the bone surface.

One phenomenon associated with ultrasonic tooling which acts to hinder the beneficial effects of irrigating the operative site is ultrasonic atomization. When an ultrasonically vibrating body is brought into contact with fluid, that fluid is broken into small droplets which have a size inversely proportional to the frequency of vibration. In other words, the higher the frequency, the smaller and more mobile the liquid drop. Droplets created by ultrasonic vibrations can be very small in size, with some being less than 1 micron in diameter. This phenomenon is well known to the art. In fact, many devices intended to atomize liquid, such as room humidifiers, medical nebulizers, and industrial spray nozzle are based upon this principle. In the operating theater, however, the presence of nebulized particles is not appreciated, since these particles may contain viral or bacterial agents. Also, some of the fluid will be atomized before reaching the operative site, reducing the cooling efficiency. An effective way to insure the liquid transport is needed.

Two devices were developed to solve these issues. These devices are described in U.S. Pat. Nos. 6,379,371 and 6,443,969. The blades of these patents are extremely effective not only in maxillofacial applications as described above but also in other applications involving bone cutting as well.

One limitation of these blades is that the blades must be advanced into the bone tissue in a plunging or brush stroke manner, with the distal tip of the blade leading. Sideways or lateral advancement of the blade after the initial cut is made has not been shown to be practical. In addition, after a cut is made, the blades can cut only tissue facing the incision. This mode of operation is not advantageous in cases were extremely sensitive tissue, such as brain or spinal cord tissue, is beneath the bone.

OBJECTS OF THE INVENTION

It is an object of the present invention to provide an improved ultrasonic cutting blade of the above-described type.

Another object of the present invention is to provide an ultrasonic cutting blade that, in addition to cutting in a forward or distal direction away from the user, is effectively able to cut laterally, that is, in a direction substantially perpendicular to the axis of the blade and thus substantially perpendicular to the direction of propagation of ultrasonic compression waves.

A further object of the present invention is to provide an ultrasonic cutting blade that, in addition to cutting in a forward or distal direction away from the operator of the instrument, is able to cut backwards, that is in a proximal direction towards the operator.

These and other objects of the present invention will be apparent from the drawings and detailed descriptions herein. While every object of the invention is believed to be attained in at least one embodiment of the invention, there is not necessarily any single embodiment that achieves all of the objects of the invention.

SUMMARY OF THE INVENTION

The present invention provides an improved blade for use with ultrasonic cutting instruments. An embodiment of an ultrasonic cutting blade pursuant to the present invention allows thin kerf cuts, does not require predrilled holes for cutting, allows complex geometric cuts, has a continuous cutting edge, and has a hook feature that enables backward cutting, that is, cutting in a proximal direction towards the operator or user. The blade accommodates liquid irrigation at the blade/tissue interface for reducing and limiting thermal damage to living tissue. The present invention specifically targets the application of cutting viable bones in surgery, although the device is not exclusive to this application.

An ultrasonic surgical blade comprises, in accordance with the present invention, a blade body and a shank. The shank is fixed at one end to the blade body and is operatively connectable at an opposite end to a source of ultrasonic vibrations. The shank has a longitudinal axis. The blade body is eccentrically disposed relative to the axis. The blade body includes an elongate portion oriented substantially parallel to the axis and further includes a distal end portion at an end of the elongate portion opposite the shank. The distal end portion of the blade body has a cutting edge facing in a distal direction away from the shank, while the elongate portion has a cutting edge facing laterally away from the axis.

Typically, the shank has a shank width in a direction substantially perpendicular to the axis, the blade body has a blade width in a direction substantially perpendicular to the axis, and the blade width is substantially less than the shank width. Moreover, the blade body has a thickness substantially less than the blade width.

Pursuant to further features of the present invention, the distal end portion of the blade body is a hook portion, while the blade body and the shank define a cutout or recess between the shank at a proximal end and the hook portion at the distal end of the blade body.

Pursuant to another feature of the present invention, the elongate portion of the blade body is located entirely to one side of the axis. The elongate portion may include a first edge and a second edge substantially parallel to one another and to the axis, at least one of the first edge and the second edge including a blunt section. Alternatively or additionally, at least one of the first edge and the second edge includes a sharp section.

It is contemplated that the hook portion is provided with an arcuate cutting edge facing in a distal direction, away from the shank, and with an additional cutting edge facing in a proximal direction, toward the shank. The hook shaped distal end portion of the blade body may be further provided with a notch facing in a proximal direction and toward the shank. The arcuate cutting edge and/or the additional cutting edge may be a blunt edge. In particular embodiments of the present invention, the arcuate cutting edge extends through an arc of 180 degrees or 90 degrees.

The cutout or recess may be substantially rectangular.

The blade body may include an outwardly facing substantially J-shaped cutting edge.

Pursuant to one embodiment of the present invention, an ultrasonic surgical blade has at least three cutting edges including (1) an outwardly facing cutting edge with a first linear section extending substantially parallel to the axis of the shank and an arcuate section along the distal end of the blade body, (2) a rearwardly facing cutting edge defined by the hooked distal end portion of the blade body, and (3) a second linear section opposite the first linear section. Where the elongate portion of the blade body is disposed to one side of the axis, the second linear section faces the axis. Preferably, the entire blade body including three cutting edges is disposed in a single plane. The outwardly facing linear section and the arcuate section are continuous with one another to form a single smooth cutting edge. The arcuate section may comprise various sector angles and is disposed on the blade body substantially opposite the shank.

The straight or linear cutting sections are longitudinal and oriented substantially parallel to the axis of the blade. In at least one embodiment of the ultrasonic cutting blade, the elongate portion of the blade is tapered, the outwardly facing cutting edge extending at a slight angle relative to the axis.

The edges of the linear sections do not necessarily have to have the same sharpness. For instance, the outer longitudinal edge may be sharp and the inner edge may be blunt, or vice versa.

The shank is preferably provided with an axially extending bore for the conveyance of cooling fluid to the blade body. The blade body is preferably provided at an end opposite the shank with a recess communicating with the bore for distributing fluid from the slot towards the cutting edge. The recess preferably has a configuration that parallels at least a portion of the cutting edge. Where the cutting edge is circular and the blade body has a planar surface between the fluid distribution guide surface and the cutting edge, for instance, the recess has a fluid distribution surface inclined with respect to the planar blade surface and extending along a circular arc.

The cutting edges of a blade in accordance with the present invention are generally continuous, i.e., have no teeth, serrations or voids. This continuity provides a smooth contact surface essential when making precise cuts. In contrast, in an ultrasonic cutting blade having teeth, serrations or interruptions, the feel of the instrument changes and the instrument is more difficult to guide as the teeth, serrations, or interruptions are moved across the bone at the surgical site. Teeth on the blade edge not only do not improve the cutting speed but make it difficult to keep the edge on a predetermined cut line. The continuous blade edges of the present invention also give the cutting process a consistent feel to the surgeon, similar to the feel of a standard scalpel blade.

A blade in accordance with the present invention provides the user with the option of cutting sideways through a patient's tissues, that is, in a direction generally perpendicular to the axis of the blade and the shank. In addition, the user may cut tissue by pulling backward toward the proximal end of the device after hooking material on the inner hook section.

A blade in accordance with the present invention may have a particularly small width, allowing tighter radius of cuts.

A blade in accordance with the present invention results in less dead bone and a small cut kerf. This keeps the cut narrow and provides for quicker healing than if the bone were overheated to necrosis or if the cut was wider.

An ultrasonic surgical blade in accordance with the present invention may be used to perform a spinal laminectomy. In such a surgical method, an operating surgeon uses a cutting blade having a blade body and a shank, the shank being fixed at one end to the blade body, the blade body having a hook portion at a distal end and opposite the shank, the hook portion including a first cutting edge facing in a distal direction away from the shank and a second cutting edge facing in a proximal direction toward the shank. The method comprises (a) operatively connecting the shank at an end opposite the blade body to a source of ultrasonic vibrations, (b) thereafter moving the blade into a patient, (c) ultrasonically vibrating the blade during the moving of the blade into the patient, so that the first cutting edge cuts into tissues of the patient, (d) subsequently pulling the blade in a proximal direction out of the patient so that the second cutting edge engages bony tissue of the patient, and (e) ultrasonically vibrating the blade during the pulling of the blade to thereby cut through the bony tissue.

The shank may have a longitudinal axis, while the blade body includes an elongate portion connecting the shank to the hook portion, the elongate portion including a third cutting edge facing the axis. In that event, pursuant to another feature of the present invention, the method further comprises shifting the blade body laterally after the moving of the blade into the patient and prior to the pulling of the blade in a proximal direction out of the patient, and ultrasonically vibrating the blade during the shifting of the blade to thereby enable the third cutting edge to cut through tissues of the patient.

The elongate portion of the blade body is preferably disposed entirely to one side of the axis, and the vibrating of the blade during the shifting of the blade comprises vibrating the elongate portion at least partially in a direction orthogonal to the axis. The eccentric placement of the blade body relative to the shank serves to generate a transverse vibration waveform when the excitation waveform passing into the shank of the blade is entirely a longitudinal compression wave.

In the case of a spinal laminectomy, the bony tissue is a spinal lamina.

DETAILED DESCRIPTION

Figure 1:
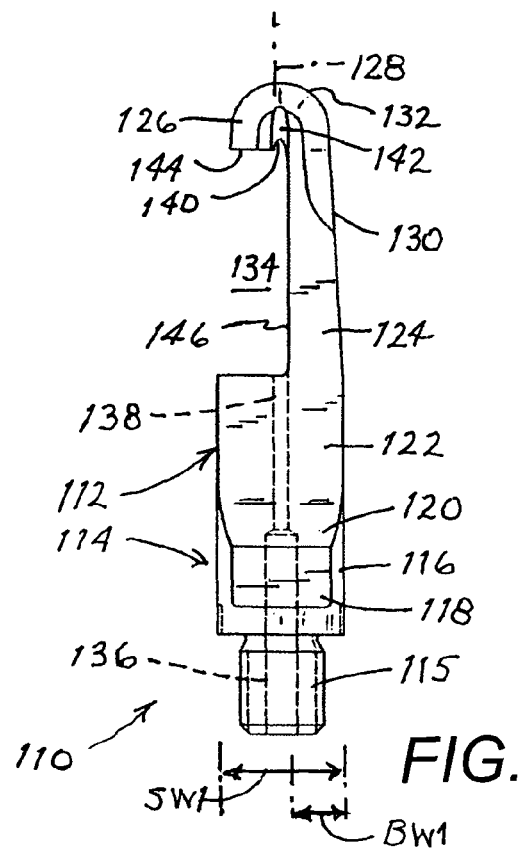
FIG. 1 is a side elevational view of an ultrasonic surgical blade in accordance with the present invention.

As depicted in FIG. 1, an ultrasonic surgical blade 110 comprises a blade body 112 and a shank 114. Shank 114 is fixed at one end to blade body 112 and is provided at an opposite end with an externally threaded neck 115 for connecting blade 110 to a source of ultrasonic vibrations (not shown). Shank 114 includes a cylindrical body 116 provided on opposing sides with a pair of planar surfaces 118 engageable by a wrench for alternatively tightening and loosening the blade from the source of ultrasonic vibrations. Shank 118 is formed at a distal end with a pair of inclined surfaces 120 that smoothly connect to blade body 112.

Blade body 112 includes a proximal plate shaped portion 122, an elongate longitudinal portion 124, and a hook-shaped distal end portion 126 all integrally continuously formed with each other. Blade body 112 is eccentrically disposed relative to a longitudinal axis 128 of blade 110 and particularly of shank 114. Elongate blade portion 124 is slightly tapered and oriented substantially parallel to axis 128. An outer elongate cutting edge section 130 of elongate blade portion 124 is slightly inclined relative to axis 128 and is continuous at a distal end with a circularly arcuate cutting edge 132 defining a distal periphery of hook-shaped distal end portion 126.

Blade body 112 is eccentrically disposed relative to axis 128 in that elongate or longitudinal blade portion 124 is disposed entirely to one side of the axis. During use of blade 110, this eccentricity is believed to convert a portion of the energy of longitudinal ultrasonic compression waves into ultrasonic transverse waves, whereby elongate or longitudinal blade portion 124 exhibits a motion component oriented substantially transversely to axis 128 and cutting edge 130. It is believed that this transverse motion enhances a lateral cutting action of edge 130, in a direction generally transversely to axis 128. Where an ultrasonic cutting blade is symmetrically formed as disclosed in U.S. Pat. Nos. 6,379,371 and 6,443,969, the cutting action is generally limited to a forward or distal side of the blade (cutting edge 132 in FIG. 1).

Plate shaped blade portion 122, elongate longitudinal blade portion 124, and hook-shaped distal end portion 126 together define a cutout or recess 134 between shank 114 at a proximal end and hook portion 126 at the distal end of blade body 112. Cutout or recess 134 is substantially but not perfectly rectangular, owing to the tapered aspect of blade body 112 and more particular to distal end portion 126 having a smaller transverse dimension or width than proximal plate shaped portion 122.

A bore or channel 136 provided in shank 114 communicates at a distal end with a narrower bore or channel 138 in proximal blade portion 122. Channel 138 in turn communicates with recess 134. Channels 136 and 138 deliver irrigating and cooling liquid to recess 134 for distribution over blade body 112. To that end, a cutout or notch 140 and a liquid distribution surface 142 are provided in hook-shaped distal end portion 126 of blade body 112 for assisting in the conduction of a coolant liquid to cutting edge 132.

Distal end portion 126 of blade body 112 has a cutting edge 144 facing in a proximal direction toward from shank 114, while elongate blade portion 124 has a cutting edge 146 facing laterally toward from axis 128. Cutting edge 144 is sharp while cutting edge 146 is blunt, having the thickness of blade body 112 along the elongate longitudinal portion 124 thereof. Cutout or notch 140 has an edge (not separated enumerated) with a substantially smaller radius of curvature than any radius of curvature of cutting edge 144.

Shank 114 has a shank width SW1 in a direction substantially perpendicular to axis 128, while elongate portion 124 of blade body 112 has a width BW1 also measured in a direction substantially perpendicular to axis 128. Blade width BW1 is substantially less than shank width SW1, which facilitates the eccentric disposition of blade body 112 relative to shank 114. Blade body 112 has a thickness (not shown) substantially less than blade width BW1.

Arcuate cutting edge 132 of distal end portion 126 extends through an arc of 180 degrees in the embodiment of FIG. 1. Cutting edges 132 and 130 together define an outwardly facing substantially J-shaped cutting edge (not separately labeled). Ultrasonic surgical blade 110 thus has several cutting edges including (1) this outwardly facing J-shaped cutting edge with a linear section 130 and arcuate section 132, (2) rearwardly facing cutting edge 144, and (3) linear section 146 facing inwardly or oppositely to cutting edge 130. Arcuate section 132 may comprise various sector angles and is disposed on the blade body substantially opposite shank 114.

The straight or linear cutting sections or edges 130 and 146 are longitudinal and oriented substantially parallel to the axis 128 of blade 110. Elongate portion 124 of blade body 112 is tapered, the outwardly facing cutting edge 130 extending at an angle of 5-15 degrees relative to axis 128.

Cutting edges 130 and 146 do not necessarily have to have the same sharpness. For instance, the outer longitudinal edge 130 may be sharp and the inner edge 146 may be blunt, or vice versa.

Cutting edges 130, 132, 144, 146 of blade 110 are continuous (except for notch 140), i.e., have no teeth, serrations or voids. This continuity provides a smooth contact surface essential when making precise cuts.

Figure 2:
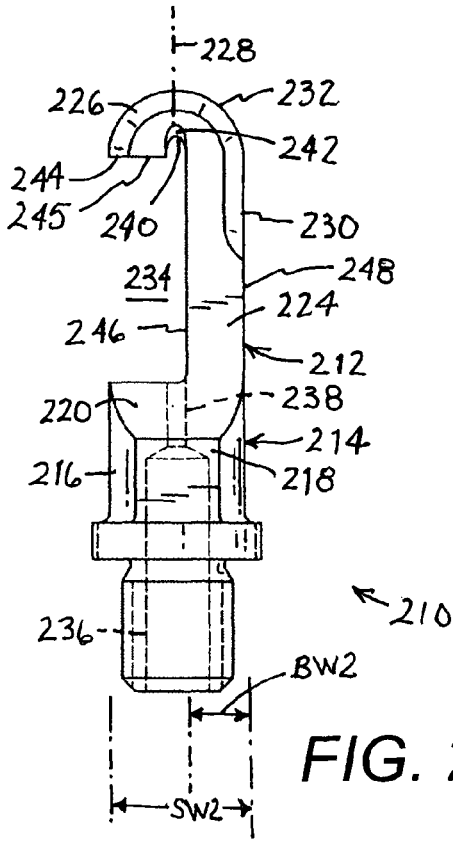
FIG. 2 is a side elevational view of another ultrasonic surgical blade in accordance with the present invention.

FIG. 2 depicts another ultrasonic surgical blade 210 comprising a blade body 212 and a shank 214. Shank 214 is fixed at one end to blade body 212 and is provided at an opposite end with an externally threaded neck 215 for connecting blade 210 to a source of ultrasonic vibrations (not shown). Shank 214 includes a cylindrical body 216 provided on opposing sides with a pair of planar surfaces 218 engageable by a wrench for alternatively tightening and loosening the blade from the source of ultrasonic vibrations. Shank 218 is formed at a distal end with a pair of inclined surfaces 220 that smoothly connect to blade body 212.

Blade body 212 does not include a proximal plate shaped portion like proximal plate shaped portion 122 of blade body 112. Instead, shank 214 is directly continuous with an elongate longitudinal portion 224 of blade body 212.

Blade body 212 further includes a hook-shaped distal end portion 226 integrally continuously formed with elongate blade portion 224. Blade body 212 is eccentrically disposed relative to a longitudinal axis 228 of blade 210 and particularly of shank 214, owing to a staggered lateral disposition of elongate portion 224 relative to shank 214. During use of blade 210, this eccentricity is believed to convert a portion of the energy of longitudinal ultrasonic compression waves into ultrasonic transverse waves, whereby elongate or longitudinal blade portion 224 exhibits a motion component oriented substantially transversely to axis 228 and cutting edge 230. It is believed that this transverse motion enhances a lateral cutting action of edge 230, in a direction generally transversely to axis 228.

Elongate blade portion 224 is rectangular and has a uniform width BW2. Elongate blade portion 224 is oriented substantially parallel to axis 228. An outer elongate cutting edge section 230 of elongate blade portion 224 is parallel to axis 228 and is continuous at a distal end with a circularly arcuate cutting edge 232 defining a distal periphery of hook-shaped distal end portion 226.

The distal end of shank 214, elongate longitudinal blade portion 224, and hook-shaped distal end portion 226 together define a rectangular cutout or recess 234 between shank 214 at a proximal end and hook portion 226 at the distal end of blade body 212.

A proximal bore or channel 236 in shank 214 communicates at a distal end with a narrower bore or channel 238 in a tapered distal end (not separately labeled) of shank 214. Channel 238 in turn communicates with recess 234. Channels 236 and 238 deliver irrigating and cooling liquid to recess 234 for distribution over blade body 212. To that end, a cutout or notch 240 and a liquid distribution surface 242 are provided in hook-shaped distal end portion 226 of blade body 212 for assisting in the conduction of a coolant liquid to cutting edge 232.

Distal end portion 226 of blade body 212 has a sharp cutting edge 244 and a blunt cutting edge 245 facing in a proximal direction toward from shank 214, while elongate blade portion 224 has a blunt cutting edge 246 facing laterally toward from axis 228. Cutting edges 245 and 246 are blunt and have the thickness of blade body 212. Cutout or notch 240 has an edge (not separately designated) with a substantially smaller radius of curvature than any radius of curvature of cutting edge 244.

Shank 214 has a shank width SW2 in a direction substantially perpendicular to axis 228, while elongate portion 224 of blade body 212 has width BW2 also measured in a direction substantially perpendicular to axis 228. Blade width BW2 is substantially less than shank width SW2, which facilitates the eccentric disposition of blade body 212 relative to shank 214. Blade body 212 has a thickness (not shown) substantially less than blade width BW2.

Arcuate cutting edge 232 of distal end portion 226 extends through an arc of 180 degrees in the embodiment of FIG. 2. Cutting edges 232 and 230 together define an outwardly facing substantially J-shaped cutting edge (not separately labeled). Ultrasonic surgical blade 210 thus has several cutting edges including (1) this outwardly facing J-shaped cutting edge with a linear section 230 and arcuate section 232, (2) rearwardly facing cutting edges 244 and 245, and (3) linear section 246 facing inwardly or oppositely to cutting edge 230. On a laterally outwardly facing side, elongate blade portion 224 may also include a blunt cutting edge section 248. Arcuate section 232 may comprise various sector angles and is disposed on the blade body substantially opposite shank 214.

The straight or linear cutting sections or edges 230, 246, and 248 are longitudinal and oriented parallel to the axis 228 of blade 210. Cutting edges 230, 232, 244, 246 of blade 210 are continuous (except for notch 240), i.e., have no teeth, serrations or voids. This continuity provides a smooth contact surface essential when making precise cuts.

Figure 3:
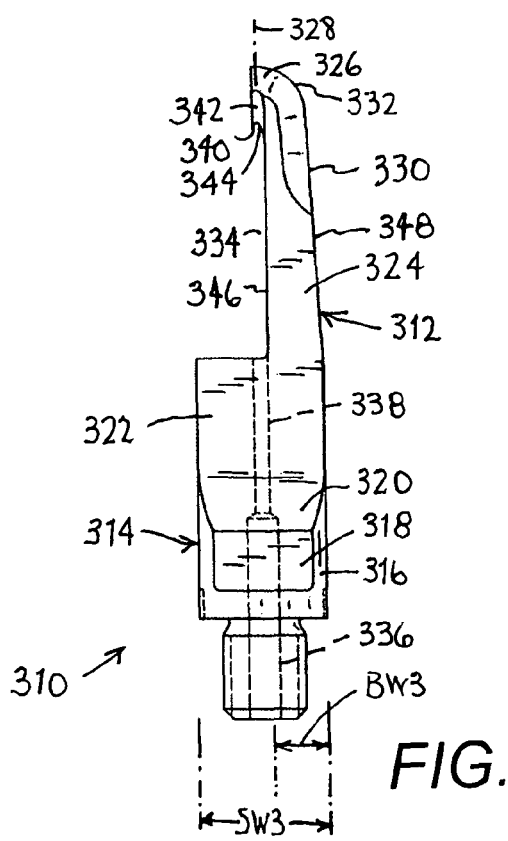
FIG. 3 is a side elevational view of a further ultrasonic surgical blade in accordance with the present invention.

As depicted in FIG. 3, an ultrasonic surgical blade 310 comprises a blade body 312 and a shank 314. Shank 314 is fixed at one end to blade body 312 and is provided at an opposite end with an externally threaded neck 315 for connecting blade 310 to a source of ultrasonic vibrations (not shown). Shank 314 includes a cylindrical body 316 provided on opposing sides with a pair of planar surfaces 318 engageable by a wrench for alternatively tightening and loosening the blade from the source of ultrasonic vibrations. Shank 318 is formed at a distal end with a pair of inclined surfaces 320 that smoothly connect to blade body 312.

Blade body 312 includes a proximal plate shaped portion 322, an elongate longitudinal portion 324, and a truncated hook-shaped distal end portion 326 all integrally continuously formed with each other. Blade body 312 is eccentrically disposed relative to a longitudinal axis 328 of blade 310 and particularly of shank 314. Elongate blade portion 324 is slightly tapered and oriented substantially parallel to axis 328. An outer elongate cutting edge section 330 of elongate blade portion 324 is slightly inclined relative to axis 328 and is continuous at a distal end with a circularly arcuate cutting edge 332 defining a distal periphery of hook-shaped distal end portion 326.

Blade body 312 is eccentrically disposed relative to axis 328 in that elongate or longitudinal blade portion 324 is disposed entirely to one side of the axis. During use of blade 310, this eccentricity is believed to convert a portion of the energy of longitudinal ultrasonic compression waves into ultrasonic transverse waves, whereby elongate or longitudinal blade portion 324 exhibits a motion component oriented substantially transversely to axis 328 and cutting edge 330. It is believed that this transverse motion enhances a lateral cutting action of edge 330, in a direction generally transversely to axis 328.

Plate shaped blade portion 322, elongate longitudinal blade portion 324, and hook-shaped distal end portion 326 together define a shallow rectangular cutout or recess 334 between shank 314 at a proximal end and hook portion 326 at the distal end of blade body 312.

A bore or channel 336 provided in shank 314 communicates at a distal end with a narrower bore or channel 338 in proximal blade portion 322. Channel 338 in turn communicates with recess 334. Channels 336 and 338 deliver irrigating and cooling liquid to recess 334 for distribution over blade body 312. To that end, a notch 340 and a liquid distribution surface 342 are provided in hook-shaped distal end portion 326 of blade body 312 for assisting in the conduction of a coolant liquid to cutting edge 332.

Distal end portion 326 of blade body 312 has a cutting edge 344 facing in a proximal direction toward from shank 314, while elongate blade portion 324 has a cutting edge 346 facing laterally toward from axis 328. Cutting edge 344 is sharp (owing to the formation of notch 340 and surface 334) while cutting edge 346 is blunt, having the thickness of blade body 312 along the elongate longitudinal portion 324 thereof.

Shank 314 has a shank width SW3 in a direction substantially perpendicular to axis 328, while elongate portion 324 of blade body 312 has a width BW3 also measured in a direction substantially perpendicular to axis 328. Blade width BW3 is substantially less than shank width SW3, which facilitates the eccentric disposition of blade body 312 relative to shank 314. Blade body 312 has a thickness (not shown) substantially less than blade width BW3.

Arcuate cutting edge 332 of distal end portion 326 extends through an arc of 90 degrees in the embodiment of FIG. 3. Cutting edges 332 and 330 together define an outwardly facing substantially J-shaped cutting edge (not separately labeled). Ultrasonic surgical blade 310 thus has several cutting edges including (1) this outwardly facing J-shaped cutting edge with a linear section 330 and arcuate section 332, (2) rearwardly facing cutting edge 344, and (3) linear section 346 facing inwardly or oppositely to cutting edge 330. Also, elongate blade portion 324 may be provided with a laterally outwardly facing blunt cutting edge 348. Arcuate section 332 may comprise various sector angles and is disposed on the blade body substantially opposite shank 314.

The straight or linear cutting sections or edges 330 and 346 are longitudinal and oriented substantially parallel to the axis 328 of blade 310. Elongate portion 324 of blade body 312 is tapered, the outwardly facing cutting edge 330 extending at an angle of 5-15 degrees relative to axis 328.

Cutting edges 330, 332, 346 of blade 310 are continuous (except for notch 340), i.e., have no teeth, serrations or voids. This continuity provides a smooth contact surface essential when making precise cuts.

Figure 4:
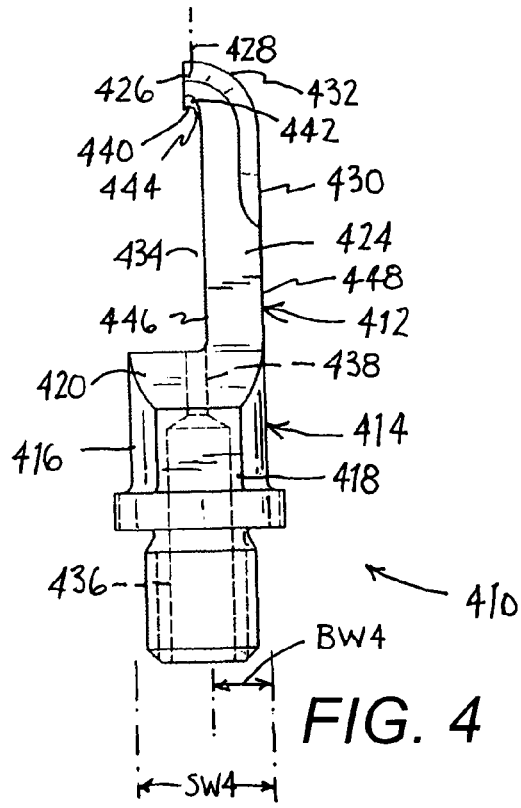
FIG. 4 is a side elevational view of yet another ultrasonic surgical blade in accordance with the present invention.

As shown in FIG. 4, yet another ultrasonic surgical blade 410 comprises a blade body 412 and a shank 414. Shank 414 is fixed at one end to blade body 412 and is provided at an opposite end with an externally threaded neck 415 for connecting blade 410 to a source of ultrasonic vibrations (not shown). Shank 414 includes a cylindrical body 416 provided on opposing sides with a pair of planar surfaces 418 engageable by a wrench for alternatively tightening and loosening the blade from the source of ultrasonic vibrations. Shank 418 is formed at a distal end with a pair of inclined surfaces 420 that smoothly connect to blade body 412.

Blade body 412 does not include a proximal plate shaped portion like proximal plate shaped portion 142 of blade body 112. Instead, shank 414 is directly continuous with an elongate longitudinal portion 424 of blade body 412.

Blade body 412 further includes a truncated hook-shaped distal end portion 426 integrally continuously formed with elongate blade portion 424. Blade body 412 is eccentrically disposed relative to a longitudinal axis 428 of blade 410 and particularly of shank 414, owing to a staggered lateral disposition of elongate portion 424 relative to shank 414 and axis 428. During use of blade 410, this eccentricity is believed to convert a portion of the energy of longitudinal ultrasonic compression waves into ultrasonic transverse waves, whereby elongate or longitudinal blade portion 424 exhibits a motion component oriented substantially transversely to axis 428 and cutting edge 430. It is believed that this transverse motion enhances a lateral cutting action of edge 430, in a direction generally transversely to axis 428.

Elongate blade portion 424 is rectangular and has a uniform width BW2. Elongate blade portion 424 is oriented substantially parallel to axis 428. An outer elongate cutting edge section 430 of elongate blade portion 424 is parallel to axis 428 and is continuous at a distal end with a circularly arcuate cutting edge 432 defining a distal periphery of hook-shaped distal end portion 426.

The distal end of shank 414, elongate longitudinal blade portion 424, and hook-shaped distal end portion 426 together define a shallow or thin rectangular cutout or recess 434 between shank 414 at a proximal end and hook portion 426 at the distal end of blade body 412.

A proximal bore or channel 436 in shank 414 communicates at a distal end with a narrower bore or channel 438 in a tapered distal end (not separately labeled) of shank 414. Channel 438 in turn communicates with recess 434. Channels 436 and 438 deliver irrigating and cooling liquid to recess 434 for distribution over blade body 412. To that end, a notch 440 and a liquid distribution surface 442 are provided in hook-shaped distal end portion 426 of blade body 412 for assisting in the conduction of a coolant liquid to cutting edge 432.

Distal end portion 426 of blade body 412 has a sharp cutting edge 444 (owing to the formation of notch 440 and surface 434) facing in a proximal direction toward from shank 414, while elongate blade portion 424 has a blunt cutting edge 446 facing laterally toward from axis 428. Cutting edge 446 is blunt and has the thickness of blade body 412.

Shank 414 has a shank width SW4 in a direction substantially perpendicular to axis 428, while elongate portion 424 of blade body 412 has width BW4 also measured in a direction substantially perpendicular to axis 428. Blade width BW4 is substantially less than shank width SW4, which facilitates the eccentric disposition of blade body 412 relative to shank 414. Blade body 412 has a thickness (not shown) substantially less than blade width BW4.

Arcuate cutting edge 432 of distal end portion 426 extends through an arc of 90 degrees in the embodiment of FIG. 4. Cutting edges 432 and 430 together define an outwardly facing substantially J-shaped cutting edge (not separately labeled). Ultrasonic surgical blade 410 thus has several cutting edges including (1) this outwardly facing J-shaped cutting edge with a linear section 430 and arcuate section 432, (2) rearwardly facing cutting edges 444 and 445, and (3) linear section 446 facing inwardly or oppositely to cutting edge 430. On a laterally outwardly facing side, elongate blade portion 424 may also include a blunt cutting edge section 448. Arcuate section 432 may comprise various sector angles and is disposed on the blade body substantially opposite shank 414.

The straight or linear cutting sections or edges 430, 446, and 448 are longitudinal and oriented parallel to the axis 428 of blade 410. Cutting edges 430, 432, 446 of blade 410 are continuous (except for notch 440), i.e., have no teeth, serrations or voids. This continuity provides a smooth contact surface essential when making precise cuts.

Ultrasonic surgical blade 110, 210, 310, and 410 are particularly suited for performing a spinal laminectomy. Shank 114, 214, 314, 414 is connected at an end opposite blade body 112, 212, 312, 412 to a source of ultrasonic vibrations (not shown). Thereafter blade 110, 210, 310, 410 is moved into a patient, the blade being ultrasonically vibrated during this movement, so that cutting edge 132, 232, 332, 432 cuts into tissues of the patient. Subsequently the surgeon pulls the blade 110, 210, 310, 410 in a proximal direction out of the patient so that cutting edge 144, 244, 344, 444 engages bony tissue of the patient. Blade 110, 210, 310, 410 is ultrasonically vibrated during the pulling of the blade against the bony tissue to thereby enable the cutting of the bony tissue by cutting edge 144, 244, 344, 444.

The blade body 112, 212, 312, 412 is shifted laterally after the insertion or moving of the blade 110, 210, 310, 410 into the patient and prior to the pulling of the blade in a proximal direction out of the patient. The blade 110, 210, 310, 410 is nd ultrasonically vibrated during the lateral shifting of the blade to thereby enable cutting edge 146, 246, 346, 446 to cut through tissues of the patient as required. Owing to the eccentric disposition of elongate blade portion 124, 224, 324, 424, for instance, entirely to one side of the shank axis 128, 228, 328, 428, a transmission of a longitudinal ultrasonic compression wave into the blade 110, 210, 310, 410 via shank 114, 214, 314, 414 during the shifting of the blade gives rise to a transverse ultrasonic shear wave that vibrates elongate blade portion 124, 224, 324, 424 in a direction orthogonal to the axis. Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. An ultrasonic surgical blade comprising a blade body and a shank, the shank being fixed at one end to the blade body and operatively connectable at an opposite end to a source of ultrasonic vibrations, the shank having a longitudinal axis, the shank having a shank width in a direction substantially perpendicular to the axis, the blade body having a hook portion and an elongate portion connecting said hook portion to said shank, said elongate portion having a blade width in a direction substantially perpendicular to the axis, the blade width being substantially less than the shank width, said elongate portion of the blade body having a thickness substantially less than the blade width, the blade body having said hook portion at a distal end and opposite the shank, the blade body and the shank defining a cutout or recess between the shank at a proximal end and the hook portion at the distal end of the blade body, the shank being formed with a longitudinal bore or channel communicating directly with the cutout or recess at a proximal end thereof, the blade body including the hook portion and an elongate portion located entirely to one side of the axis, the elongate portion including a first edge and a second edge substantially parallel to one another and to the axis, at least one of the first edge and the second edge including a sharp section.

2. The surgical blade defined in claim 1 wherein the blade body is eccentrically disposed relative to the axis.

3. The surgical blade defined in claim 1 wherein at least one of the first edge and the second edge includes a blunt section.

4. An ultrasonic surgical blade comprising a blade body and a shank, the shank being fixed at one end to the blade body and operatively connectable at an opposite end to a source of ultrasonic vibrations, the shank having a longitudinal axis, the shank having a shank width in a direction substantially perpendicular to the axis, the blade body having a hook portion and an elongate portion connecting said hook portion to said shank, said elongate portion having a blade width in a direction substantially perpendicular to the axis, the blade width being substantially less than the shank width, said elongate portion of the blade body having a thickness substantially less than the blade width, the blade body having said hook portion at a distal end and opposite the shank, the blade body and the shank defining a cutout or recess between the shank at a proximal end and the hook portion at the distal end of the blade body, the hook portion being provided with an arcuate cutting edge facing in a distal direction, away from the shank.

5. The surgical blade defined in claim 4 wherein the hook portion is provided with an additional cutting edge facing in a proximal direction, toward the shank.

6. The surgical blade defined in claim 5 wherein at least one of the arcuate cutting edge and the additional cutting edge is a blunt edge.

7. The surgical blade defined in claim 4 wherein the arcuate cutting edge extends through an arc taken from the group consisting of 180 degrees and 90 degrees.

8. The surgical blade defined in claim 1 wherein the hook portion is provided with a cutting edge facing in a proximal direction toward the shank.

9. The surgical blade defined in claim 8 wherein the hook portion is further provided with a notch facing in a proximal direction and toward the shank.

10. The surgical blade defined in claim 1 wherein the blade body includes an outwardly facing substantially J-shaped cutting edge.

11. An ultrasonic surgical blade comprising a blade body and a shank, the shank being fixed at one end to the blade body and operatively connectable at an opposite end to a source of ultrasonic vibrations, the shank having a longitudinal axis, the shank having a shank width in a direction substantially perpendicular to the axis, the blade body having a blade width in a direction substantially perpendicular to the axis, the blade width being substantially less than the shank width, the blade body having a thickness substantially less than the blade width, the blade body having a hook portion at a distal end and opposite the shank, the blade body and the shank defining a cutout or recess between the shank at a proximal end and the hook portion at the distal end of the blade body, the hook portion being provided with a cutting edge facing in a proximal direction toward the shank, the cutting edge being provided with a cutout or notch facing in a proximal direction and toward the shank.

12. The surgical blade defined in claim 11 wherein the cutout or notch is provided with a liquid distribution surface formed as an indentation or recess in the blade body extending to the cutout or notch.

13. The surgical blade defined in claim 11 wherein the cutout or notch has an edge with a substantially smaller radius of curvature than any radius of curvature of the cutting edge.

14. An ultrasonic surgical blade comprising a blade body and a shank, the shank being fixed at one end to the blade body and operatively connectable at an opposite end to a source of ultrasonic vibrations, the shank having a central longitudinal axis, the shank having a shank width in a direction substantially perpendicular to the axis, the blade body having a blade width in a direction substantially perpendicular to the axis, the blade width being substantially less than the shank width, the blade body having a thickness substantially less than the blade width, the blade body having a hook portion at a distal end and opposite the shank, the blade body and the shank defining a cutout or recess between the shank at a proximal end and the hook portion at the distal end of the blade body, the blade body including the hook portion and an elongate portion, the elongate portion being located entirely to one side of the axis, the elongate portion having a first straight edge extending parallel to and facing the longitudinal axis, the hook portion having a second straight edge on a side of the longitudinal axis opposite the elongate portion, the second straight edge extending parallel to and facing away from the longitudinal axis.

15. The surgical blade defined in claim 14 wherein the hook portion is formed with a notch and a recessed liquid distribution surface on a proximal side, facing the shank.

16. An ultrasonic surgical blade comprising a blade body and a shank, the shank being fixed at one end to the blade body and operatively connectable at an opposite end to a source of ultrasonic vibrations, the shank having a longitudinal axis, the blade body consisting essentially of a proximal plate shaped portion, an elongate longitudinal portion, and a distal hook portion, the longitudinal portion connecting the proximal plate shaped portion and the hook portion, the longitudinal portion being disposed entirely to one side of the axis, the hook portion extending from a distal end of the longitudinal portion towards the axis, the blade body having a cutout or recess defined by the proximal plate shaped portion at a proximal side, the hook portion at a distal side and the longitudinal portion therebetween, the hook portion being formed with a sharp circularly arcuate cutting edge facing in a distal direction and away from the shank, the longitudinal portion of the blade body being provided with a sharp linear cutting edge facing laterally away from the axis, the linear cutting edge being smoothly continuous with the circularly arcuate cutting edge in a J-shaped formation having no teeth, serrations or voids.

17. The surgical blade defined in claim 16 wherein the shank and the plate shaped portion of the blade body are formed with a longitudinal bore or channel communicating with the cutout or recess at a proximal end thereof.

18. The surgical blade defined in claim 16 wherein the arcuate cutting edge extends through an arc taken from the group consisting of 180 degrees and about 90 degrees.

19. The surgical blade defined in claim 16 wherein the hook portion is provided with a proximally facing cutting edge and a cutout or notch adjacent the proximally facing cutting edge.

* * * * *